(12) United States Patent
Lee et al.

(10) Patent No.: US 10,551,301 B2
(45) Date of Patent: Feb. 4, 2020

(54) BRIGHTNESS COLORIMETER HAVING MEASUREMENT ERROR CAUSED BY LINEARLY POLARIZED LIGHT, WHICH IS CORRECTED

(71) Applicant: ANI. Co. Ltd., Suwon-si, Gyeonggi-do (KR)

(72) Inventors: Kyu Ho Lee, Anyang-si (KR); Kyu Seok Kim, Suwon-si (KR); Sang Woo Park, Seoul (KR); Seong Cheol Ji, Siheungsi (KR); Yong Hui Park, Cheongju-si (KR); Seung Yub Choi, Anyang-si (KR)

(73) Assignee: ANI. Co. Ltd., Suwon-si, Gyeonggi-do (KR)

( * ) Notice: Subject to any disclaimer, the term of this patent is extended or adjusted under 35 U.S.C. 154(b) by 64 days.

(21) Appl. No.: 15/588,943

(22) Filed: May 8, 2017

(65) Prior Publication Data
US 2017/0370771 A1    Dec. 28, 2017

(30) Foreign Application Priority Data
Jun. 24, 2016   (KR) .................. 10-2016-0079118

(51) Int. Cl.
*G01N 21/25*     (2006.01)
*G01J 3/50*      (2006.01)
(Continued)

(52) U.S. Cl.
CPC ............ *G01N 21/251* (2013.01); *G01J 3/465* (2013.01); *G01J 3/502* (2013.01); *G01J 3/506* (2013.01); *G01J 3/513* (2013.01); *G01N 21/255* (2013.01)

(58) Field of Classification Search
CPC .... G01J 3/46; G01J 3/462; G01J 3/463; G01J 3/465; G01J 3/50; G01J 3/501;
(Continued)

(56) References Cited

U.S. PATENT DOCUMENTS

| 2,607,272 | A | * | 8/1952 | Bond | ................... | G02B 5/3083 |
| | | | | | | 359/487.06 |
| 3,924,930 | A | * | 12/1975 | Dewhirst | ............. | G02B 5/3083 |
| | | | | | | 359/352 |

(Continued)

FOREIGN PATENT DOCUMENTS

EP        0065484 A1 * 11/1982 ................ G01J 3/51

*Primary Examiner* — Gordon J Stock, Jr.
(74) *Attorney, Agent, or Firm* — Panitch Schwarze Belisario & Nadel LLP

(57) ABSTRACT

A brightness colorimeter having a measurement error caused by linearly polarized light, which is corrected, includes: a lens module to which light irradiated from one side is input; a polarization conversion module configured to intersect the light input through the lens module to convert polarization characteristics; a spectral module provided in one unit block to reflect and intersect the light input through the polarization conversion module so as to branch the light in different three directions; filter modules arranged on progress paths of the light branched in different three direction through the spectral module to intersect monochromatic light beams having specific spectra among the light branched in the three directions; and measurement modules arranged to correspond to exit angles of the monochromatic light beams penetrated through the filter modules, to measure at least one of a brightness, a chromaticity, and an error obtained by the monochromatic light beams.

8 Claims, 7 Drawing Sheets

(51) Int. Cl.
*G01J 3/46* (2006.01)
*G01J 3/51* (2006.01)

(58) Field of Classification Search
CPC .. G01J 3/502; G01J 3/505; G01J 3/506; G01J 3/51; G01J 3/513; G01N 2021/1765; G01N 2021/1768; G01N 2021/177; G01N 2021/1772; G01N 2021/1774; G01N 2021/1776; G01N 2021/216; G01N 21/25; G01N 21/251; G01N 21/255; G01N 21/27; G01N 21/274; G01N 21/29
USPC ....... 356/364, 365, 402, 405, 406, 416–420, 356/425
See application file for complete search history.

(56) References Cited

U.S. PATENT DOCUMENTS

| | | | | |
|---|---|---|---|---|
| 4,027,949 | A * | 6/1977 | Lobb | G02F 1/0311 359/250 |
| 4,272,694 | A * | 6/1981 | Jacobs | G02F 1/37 359/329 |
| 5,432,609 | A * | 7/1995 | Sugiyama | G01J 3/36 356/405 |
| 6,529,243 | B1 * | 3/2003 | von Stein | H04N 5/235 348/340 |
| 7,382,535 | B2 * | 6/2008 | Hulsey | G02B 5/3083 359/489.07 |
| 2012/0026317 | A1 * | 2/2012 | Nakahira | H04N 7/183 348/92 |
| 2016/0231175 | A1 * | 8/2016 | Sasada | G01J 3/462 |
| 2016/0234490 | A1 * | 8/2016 | Sasada | G01J 3/462 |

\* cited by examiner

BRIGHTNESS COLORIMETER HAVING MEASUREMENT ERROR CAUSED BY LINEARLY POLARIZED LIGHT, WHICH IS CORRECTED

CROSS-REFERENCE(S) TO RELATED APPLICATION

This application claims priority of Korean Patent Application No. KR10-2016-0079118, filed on Jun. 24, 2016, in the Korean Intellectual Property Office, which is hereby incorporated by reference in its entirety.

BACKGROUND OF THE INVENTION

Field of the Invention

The present disclosure relates to a brightness colorimeter having a measurement error caused by linearly polarized light, which is corrected, and more particularly, to a brightness colorimeter which is configured to convert linearly polarized light for incident light into circularly polarized light and then measure brightness and chromaticity and has a measurement error that may occur due to incidence of the linearly polarized light.

Description of the Related Art

In general, with development of optics, a technical growth of a display device is rapidly progressed and the scope of industries using the same increases.

In recent years, in technical trends of a display device, panels having functionality such as a flexible function, a waterproof function, a transparent function and a wearable function are developed. In addition, technologies for implementing enlargement, miniaturization or super thinning have been actively developed.

In addition, a technology for improving reproducibility of an image, which has a natural function of a display device, is also a main issue. Importance thereof is still high.

Accordingly, development of a technology of measuring accurate performance of the display device as well as improvement and development of hardware of the display device are required such that a precise and improved result may be deduced in accordance with development of the hardware.

Technologies for measuring color reproductivity and brightness and adjusting white balances have been spotlighted among various scheme for measuring performance of the display device. In the related art, a point measuring colorimeter that adopts a spectroscopic method when the color reproductivity and the brightness are measured is widely implemented.

However, a general display device has a structure that intersects light emitted from a back light through a polarizer film, to change brightness of pixels by electrically adjusting a parallel direction of liquid crystals for each pixel. Thus, the linearly-polarized light may be frequently included in light irradiated through the display device, and such linearly polarized light is a cause of errors in measuring the chromaticity and the brightness.

Further, the linearly polarized light is a cause that when the chromaticity and the brightness are measured through a light source irradiated from the display device, a measurement value largely differs as arrangement of the display device is changed to a lateral direction or a longitudinal direction, and the linearly polarized light thus makes accurate measurement of the chromaticity and the brightness difficult.

Thus, a method for solving the above problems is required.

SUMMARY OF THE INVENTION

The present disclosure is conceived to solve the above problems according to the related art, and an aspect of the present disclosure is to provide a brightness colorimeter that may overcome errors in resultant values obtained by measuring the chromaticity and the brightness according to polarization characteristics of light input from an object to be measured and thus, more accurately measure the chromaticity and the brightness.

Problems of the present disclosure are not limited to the above-described problems, and yet other problems could be clearly understood by those skilled in the art with reference to the following descriptions.

A brightness colorimeter having a measurement error caused by linearly polarized light, which is corrected, according to the present disclosure, may include: a lens module to which light irradiated from one side is input; a polarization conversion module configured to intersect the light input through the lens module to convert polarization characteristics; a spectral module provided in one unit block to reflect and intersect the light input through the polarization conversion module so as to branch the light in different three directions; filter modules arranged on progress paths of the light branched in different three direction through the spectral module to intersect monochromatic light beams having specific spectra among the light branched in the three directions; and measurement modules arranged to correspond to exit angles of the monochromatic light beams passed through the filter modules, to measure at least one of a brightness, a chromaticity, and an error obtained by the monochromatic light beams.

Otherwise, a brightness colorimeter having a measurement error caused by linearly polarized light, which is corrected, according to the present disclosure, may include: a lens module to which light irradiated from one side is input; a spectral module provided in one unit block to reflect and intersect the light input through the polarization conversion module so as to branch the light in different three directions; polarization conversion modules provided on progress paths of the light branched in different three directions through the spectral module, to intersect the light branched in the different three directions; filter modules arranged on the progress paths of the light branched in different three directions via the polarization conversion modules, to convert the received light into monochromatic light beams having specific spectra; and measurement modules arranged to correspond to exit angles of the monochromatic light beams passed through the filter modules, to measure at least one of a brightness, a chromaticity, and an error obtained by the monochromatic light beams.

Further, the polarization conversion module may include a wavelength plate configured to convert the linearly polarized light into the circularly polarized light.

Otherwise, the wavelength plate may be a quarter wave plate having a predetermined thickness such that the linearly polarized light vibrating in directions that are vertical to each other generates an optical path difference of a wavelength of $\lambda/4$.

Further, the spectral module may include: a first spectral body configured to branch input light in different two directions by reflecting and intersecting the input light; and a second spectral body configured to branch the light passed through the first spectral body in different two directions by reflecting and intersecting the light, wherein distances from a point at which the light is input to the first spectral body via different three directions to the filter modules are identical to each other.

Otherwise, when the total amount of the light input to the first spectral body is 1, the total amount of the light branched in different three directions may be a third.

Further, images obtained by the monochromatic light beams passed through the filter modules may have measurement errors caused by the linearly polarized light having the same visual range.

Otherwise, the filter modules may convert the light branched in the three different directions into a spectrum corresponding to an X value, a spectrum corresponding to a Y value and a spectrum corresponding to a Z value among tri-stimulus.

A brightness colorimeter having a measurement error caused by linearly polarized light, which is corrected, according to the present disclosure for solving the above problems, may measure the chromaticity and the brightness by converting linearly polarized light into circularly polarized light, and may thus identically deduce the chromaticity and the brightness having high reliability regardless of an arrangement direction of an object to be measured.

Further, the brightness colorimeter is configured such that linearly polarized light that may be generated through a spectral body such as a prism provided in a spectral module is also converted into circularly polarized light and the converted light arrives at a measurement module, so that measurement reliability for the chromaticity and the brightness may be improved.

Effects of the present disclosure are not limited to the above-described effects, and other not-mentioned effects could be clearly understood by those skilled in the art with reference to the appended claims.

BRIEF DESCRIPTION OF THE DRAWINGS

The above and other aspects, features and advantages of certain exemplary embodiments of the present invention will be more apparent from the following description taken in conjunction with the accompanying drawings, in which.

DETAILED DESCRIPTION OF EXEMPLARY EMBODIMENTS

Figure 1:
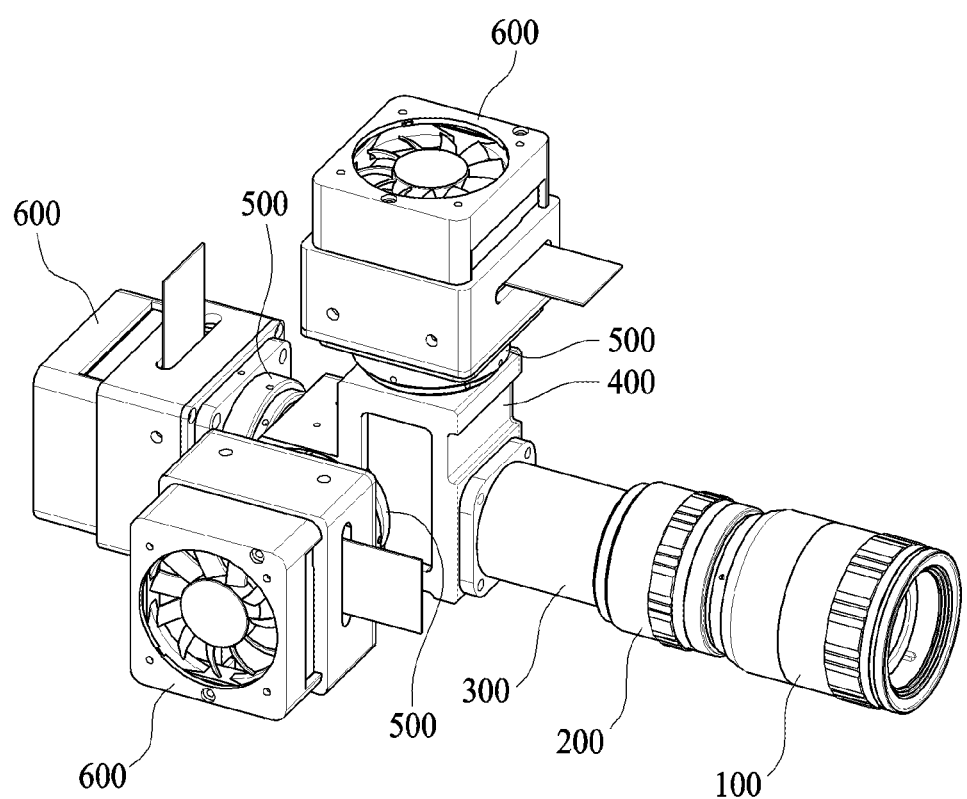
FIG. 1 is a perspective view illustrating a brightness colorimeter having a measurement error caused by linearly polarized light, which is corrected, according to an embodiment of the present disclosure.

Hereinafter, exemplary embodiments of the present disclosure, which may implement the aspects of the present disclosure in detail, will be described with reference to the accompanying drawings. In description of the present embodiment, the same elements are designated by the same names and the same reference numerals, and additional description according thereto will be omitted.

A brightness colorimeter having a measurement error caused by linearly polarized light, which is corrected, according to the present disclosure, will be implemented below.

Figure 2:
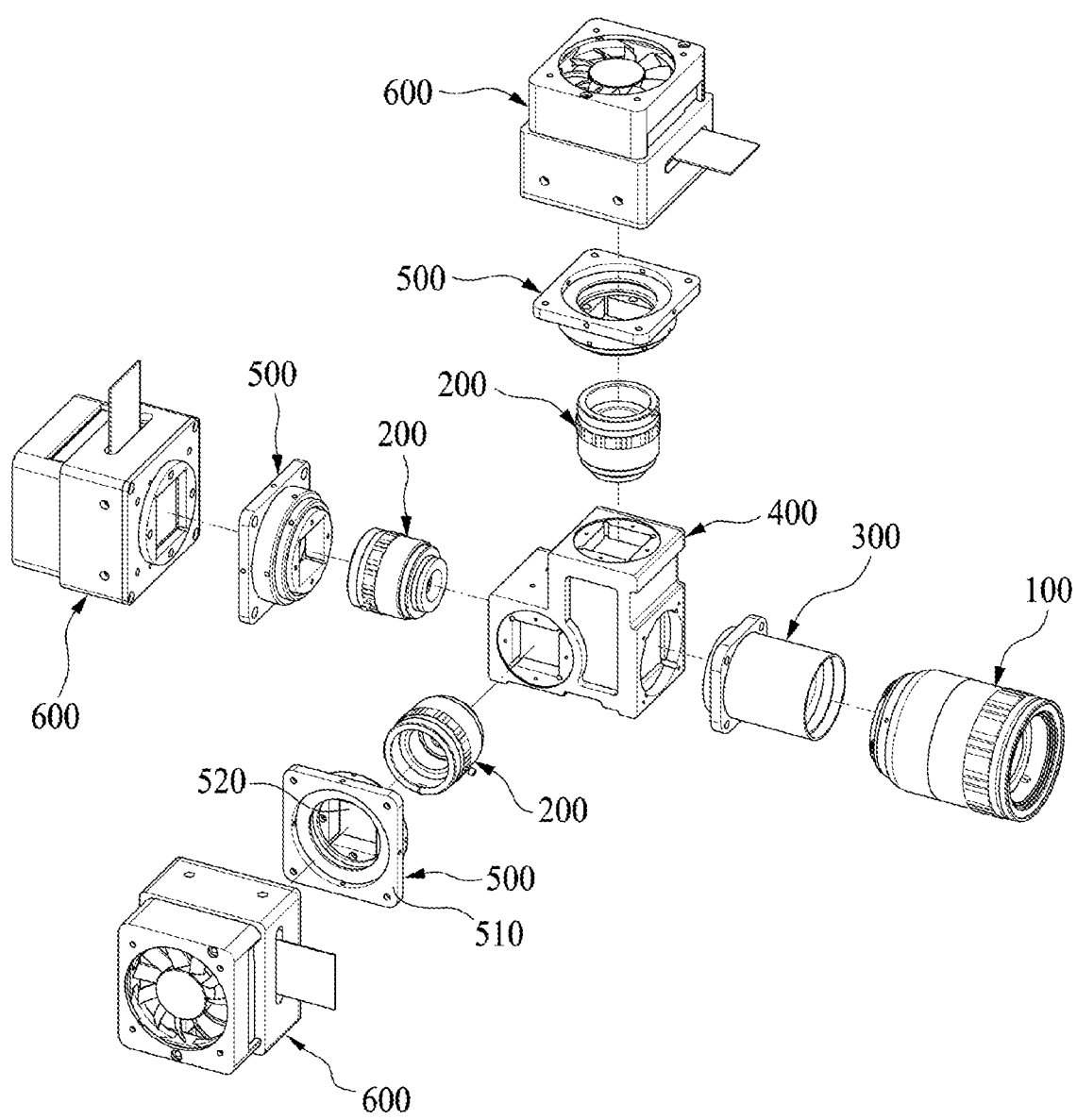
FIG. 2 is an exploded perspective view illustrating a brightness colorimeter having a measurement error caused by linearly polarized light, which is corrected, according to the embodiment of the present disclosure.
Figure 3:
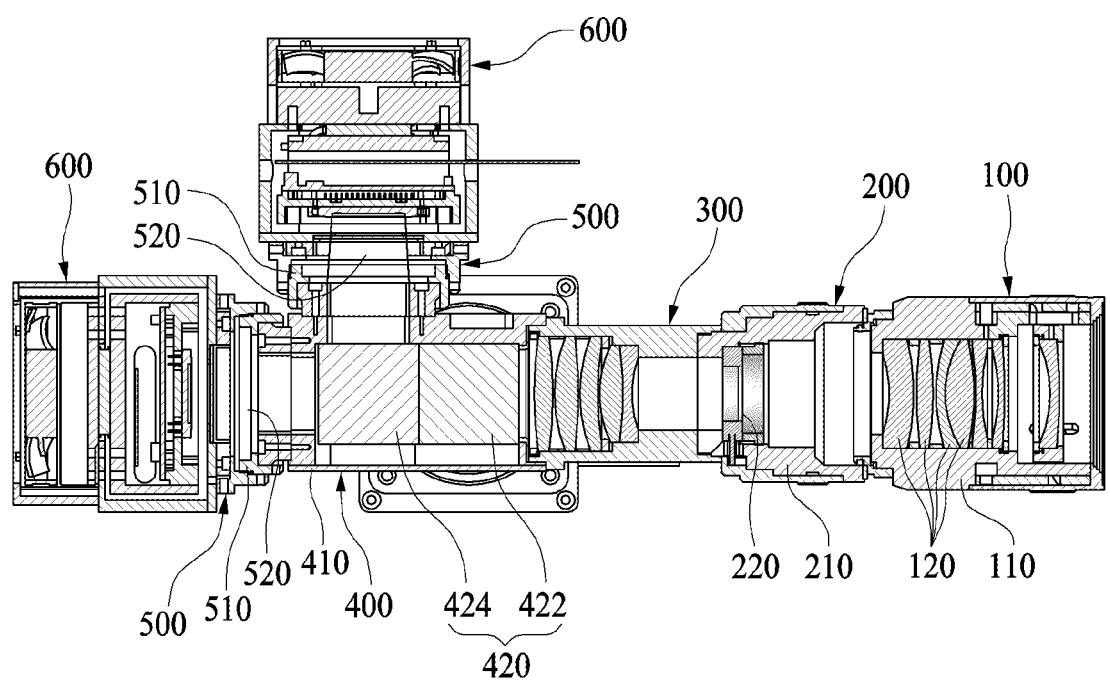
FIG. 3 is a sectional view illustrating a brightness colorimeter having a measurement error caused by linearly polarized light, which is corrected, according to the embodiment of the present disclosure.

FIG. 1 is a perspective view illustrating a brightness colorimeter having a measurement error caused by linearly polarized light, which is corrected, according to an embodiment of the present disclosure, FIG. 2 is an exploded perspective view illustrating a brightness colorimeter having a measurement error caused by linearly polarized light, which is corrected, according to the embodiment of the present disclosure, and FIG. 3 is a sectional view illustrating a brightness colorimeter having a measurement error caused by linearly polarized light, which is corrected, according to the embodiment of the present disclosure.

Referring to FIGS. 1 to 3, a brightness colorimeter having a measurement error caused by linearly polarized light, which is corrected, according to an embodiment of the present disclosure, mainly includes a lens module 100 to which light irradiated from one side is input, a polarization conversion module 200 through which light input through the lens module 100 passes to convert polarization characteristics, a spectral module 400 provided in one unit block to reflect and intersect light input through the polarization conversion module 200 to branch the light into different three paths, filter modules 500 arranged on progress paths of the light branched into the different three paths to intersect monochromatic light beams having specific spectra among the light branched into three directions, and measurement modules 600 arranged to correspond to exit angles of the monochromatic light beams passed through the filter modules 500 to measure at least one of the brightness, the chromaticity and the defect of each of the monochromatic light beams.

Otherwise, the brightness colorimeter includes a lens module 100 to which light irradiated from one side is input, a spectral module 400 provided in one unit block to reflect and intersect light input through the lens module 100 so as to branch the light into different three directions, a polarization conversion module 200 arranged on progress paths of the light branched into different three paths through the spectral module 400 to intersect the light branched into the different three directions so as to convert polarization characteristics of the light, filter modules 500 arranged on progress paths of the light branched into the different three directions through the polarization conversion module 200 to convert the received light into monochromatic light beams having specific spectra, and measurement modules 600 arranged to correspond to exit angles of the monochromatic light beams passed through the filter modules 500 to measure at least one of the brightness, the chromaticity and the defect of each of the monochromatic light beams.

Hereinafter, configurations of the above components will be described in detail.

A lens module 100 may include a plurality of lens including an object lens (objective lens), an attachment lens and the like.

In this way, the lens module 100 including the plurality of lens may be a combination formed by sequentially arranging a plurality of lens on a path of incident light.

The lens module 100 may collect light emitted from a display device that is a subject S to be measured, to project the light onto the spectral module 400 or the polarization conversion module 200, and a plurality of lens 120 are fastened to an inner circumference of the first housing 110 to be coupled to each other, so that spherical aberration, coma aberration and color aberration may be sufficiently corrected.

Such an object lens used in the lens module 100 may be a Fraunhofer type lens, a Gauss type lens and a Taylor type lens.

This is merely an example, and it is specified that the object module 100 may be implemented in various shapes and combinations according to embodiments to which the present disclosure is applied.

The brightness colorimeter according to an embodiment of the present disclosure may further include a telecentric module configured to collect light passed through the lens module 100 to improve straightness of light and a light concentrating property. The telecentric module may be arranged between the lens module 100 and the spectral module 400 or between the lens module 100 and the polarization conversion module 200, and the telecentric module may be arranged on a progress path of light that is passed through the lens module 100 and is input to the spectral module 400 or the polarization conversion module 200.

The polarization conversion module 200 may include a wavelength plate 220 restrained at an inside of the second housing 210.

The wavelength plate 220 may be implemented in a quarter wavelength plate that is a birefringent plate having a predetermined thickness such that an optical path difference corresponding to a wavelength of $\lambda/4$ is generated between linearly-polarized light vibrating in directions that are perpendicular to each other. The linearly polarized light input from one side of the wavelength plate 220 along a normal line thereof is converted into circularly polarized light and the circularly polarized light is projected into the other side of the wavelength plate 220 along the normal line thereof.

The linearly polarized light and the circularly polarized light are kinds of polarization. The linearly polarized light is light having a vibration direction of a light wave, which is direction 1 and thus having vibrations included in a plane 1 when progress of light is considered, and the circularly polarized light has a vibration direction of a light wave, which corresponds to circular vibration.

The quarter wavelength plate is configured to convert circularly polarized light into linearly polarized light or linearly polarized light into circularly polarized light to intersect the converted light, and in an embodiment of the present disclosure, is configured to convert linearly polarized light of light input via the lens module 100 from a display device that is a subject S to be measured into circularly polarized light via the polarization conversion module 200.

In a first embodiment of the present disclosure, such a polarization conversion module 200 may be arranged to be adjacent to the lens module 100 and may be configured to convert the linearly polarized light of the light input via the lens module 100 into the circularly polarized light, intersect the converted light, and transfer the passed light to the spectral module 400.

Otherwise, in a second embodiment of the present disclosure, the polarization conversion modules 200 may be arranged to be adjacent to the filter modules 500 on the paths of the light branched into the different three directions through the spectral module 400, which will be described below.

Because the three polarization conversion modules 200 are provided on the different paths to convert even linearly converted light that may be generated through an optical component such as a prism provided in the spectral module 400 as well as the linearly polarized light of the light input from the display device that is the subject S to be measured and intersect the converted light, more excellent measurement performance may be obtained as compared with the first embodiment.

The spectral module 400 is provided in one unit block and may be coupled to the lens module 100 or the polarization conversion module 200 through a barrel 300 serving as an optical path for compensating for a path of light input through the lens module 100 or the polarization conversion module 200.

The spectral module 400 may branch the light passed through the barrel 300 into different three directions by reflecting some of the light and intersecting some of the light.

Figure 4:
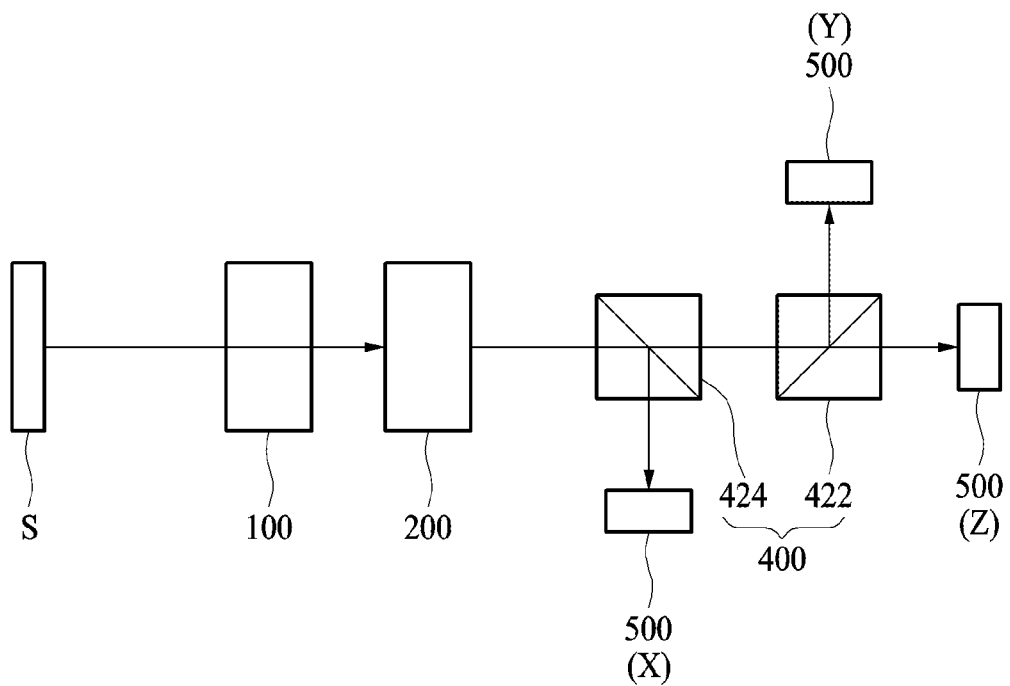
FIG. 4 is a schematic view illustrating a brightness colorimeter having a measurement error caused by linearly polarized light, which is corrected, according to the embodiment of the present disclosure.

FIG. 4 is a schematic view illustrating a brightness colorimeter having a measurement error caused by linearly polarized light, which is corrected, according to the embodiment of the present disclosure.

As illustrated in FIG. 4, the spectral module 400 may be provided in one unit block including a first spectral body 422 that reflects some of the light passed through the barrel 300 and intersect the other of the light and a second spectral body 424 that reflects some of the light passed through the first spectral body 422 and intersects the other of the light.

That is, the first spectral body 422 and the second spectral body 424 corresponding to the spectral body 420 provided in one unit block at a predetermined angle are provided, so that the light progressed along a path of the light passed through the barrel 300 may be branched into different three directions. Here, directions of the branched light may be changed depending on set angles of the first spectral body 422 and the second spectral body 424.

Here, spectral transmittances of the first spectral body 422 and the second spectral body 424 may be constantly configured in a range of 0 degree to 45 degrees.

Further, in the spectral module 400, incident surfaces of the first spectral body 422 and the second spectral body 424 at which the light input via the barrel 300 arrives and exit surfaces from which the light branched into three directions is output are provided such that incident angles and exit angles of the passed light are perpendicular to each other.

When the total amount of light input to the spectral body 420 is 1, such a spectral module 400 may branch the light into three directions and output the branched light through the exit surfaces such that an amount of each light is a third of the total amount of the light.

In addition, an incident angle of the light that is input to the spectral module 300 through the lens module 100 or the polarization conversion module 200 by the above-described telecentric module is maintained to be perpendicular to an incident surface of the spectral body 420 and straightness of light and a light concentrating property may be ensured.

Further, incident angles of the light branched in different three directions and input to the filter modules 500 via the spectral module 400 by the telecentric module may be maintained at specific angles, and the light is input while being collected.

Meanwhile, the spectral module 400 may be formed such that progress distances by which the light branched in different three directions is input to one unit block and is then output therefrom are identical to each other.

In detail, a progress distance of light reflected through the first spectral body 422, a progress distance of light passing through the first spectral body 422 and reflected through the second spectral body 424 and a progress distance of light passing through the first spectral body 422 and the second spectral body 424 may be equal to each other.

There is an advantage in that because the progress distances of the light input to the spectral module 400, branched by the spectral module 400 and output from the spectral module 400 are equal to each other, uniform imaging having the same field of view (FOV) may be acquired.

In addition, there is an advantage in that an angle of the light output from the spectral module and input to an indirect filter module through the telecentric module may be maintained constant and the light may be input to the filter modules 500 while being collected as well.

Meanwhile, the filter modules 500 may be arranged to be adjacent to the spectral module 400 or the polarization conversion module 200, which will be described, and may include three filters 520 arranged on the progress paths of the light branched in different three directions via the spectral module 400 or the polarization conversion module 200.

Such filters 520, which may be coupled to insides of fourth housings 510 and filter only the monochromatic light beams having specific spectra using an interference phenomenon occurring on a thin film, may intersect only the monochromatic light beams having specific spectra among the light branched through the spectral module 400.

Here, the monochromatic light beams filtered by the filters 520 may be included in specific spectra of X, Y and Z regions depending on tri-stimulus values according to the standard colorimetric system (CIE 1931) defined by Commission Internationale de l'Eclairage (CIE).

In more detail, the filter modules 500 may include a filter 520 through which only a monochromatic light beam having a Z value including a spectrum of 400-550 nm among the tri-stimulus values passes, a filter 520 through which only a monochromatic light beam having an Y value including a spectrum of 450-700 nm passes and a filter 520 through which only a monochromatic light beam having an X value including a spectrum of 500-700 nm passes.

The filters 520 included in the filter modules 520 should be provided such that incident light may be maintained at specific angles, and a state in which the filters 520 are provided such that the light may be maintained at specific angles is for improving measurement accuracy.

The measurement modules are arranged to correspond to exit angles of the monochromatic light beams passed through the filter modules 500, to measure the brightnesses, the chromaticities and the defects of images obtained by the monochromatic light beams.

Such measurement modules 600 may be provided such that the number thereof corresponds to the number of the filters 520, and images obtained through the measurement modules 600 may be provided to have the same field of view (FOV).

Figure 5:
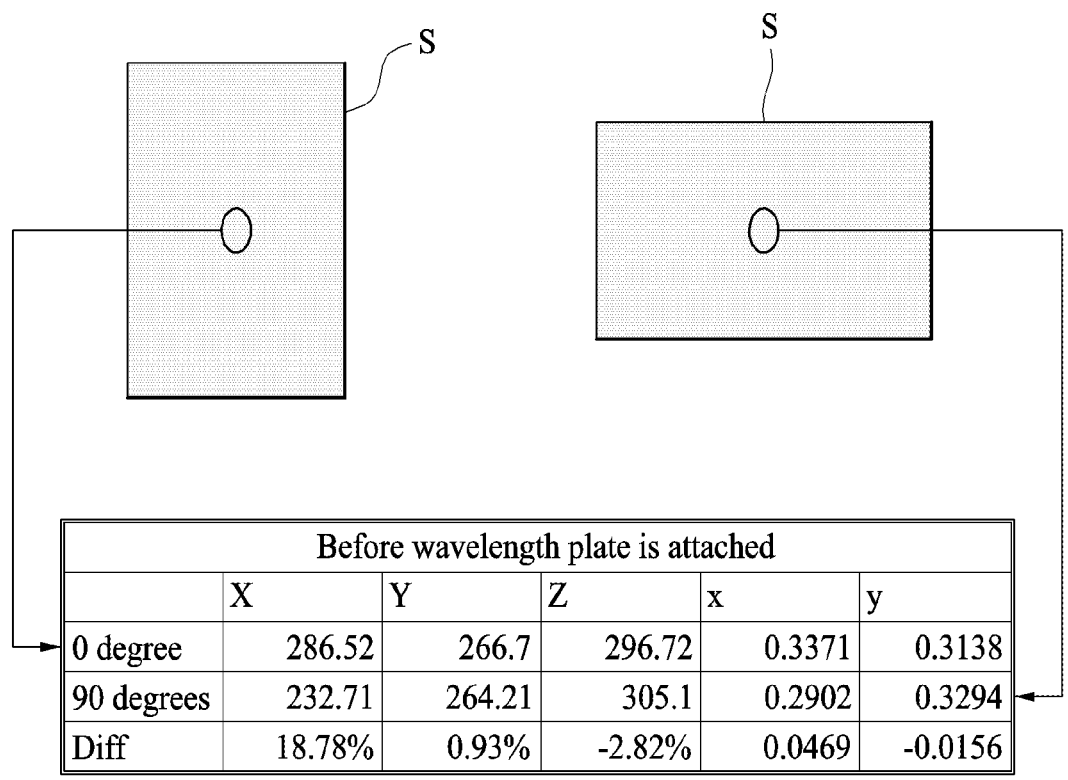
FIG. 5 is a table representing data obtained by measuring tri-stimulus values while arrangement of a subject to be measured is changed through the related art.

FIG. 5 is a table representing data obtained by measuring tri-stimulus values while arrangement of an object to be measured is changed, wherein linearly polarized light for the light irradiated through the display device that is the subject S to be measured when the display device is arranged in a longitudinal direction and linearly polarized light for the light when the display device is arranged in a transverse direction.

That is, when the chromaticity, the brightness and the defect of the display device are measured according to an embodiment of the present disclosure, a large error occurs when the same point is measured depending on an arrangement state, an arrangement angle and the like of the display device.

Figure 6:
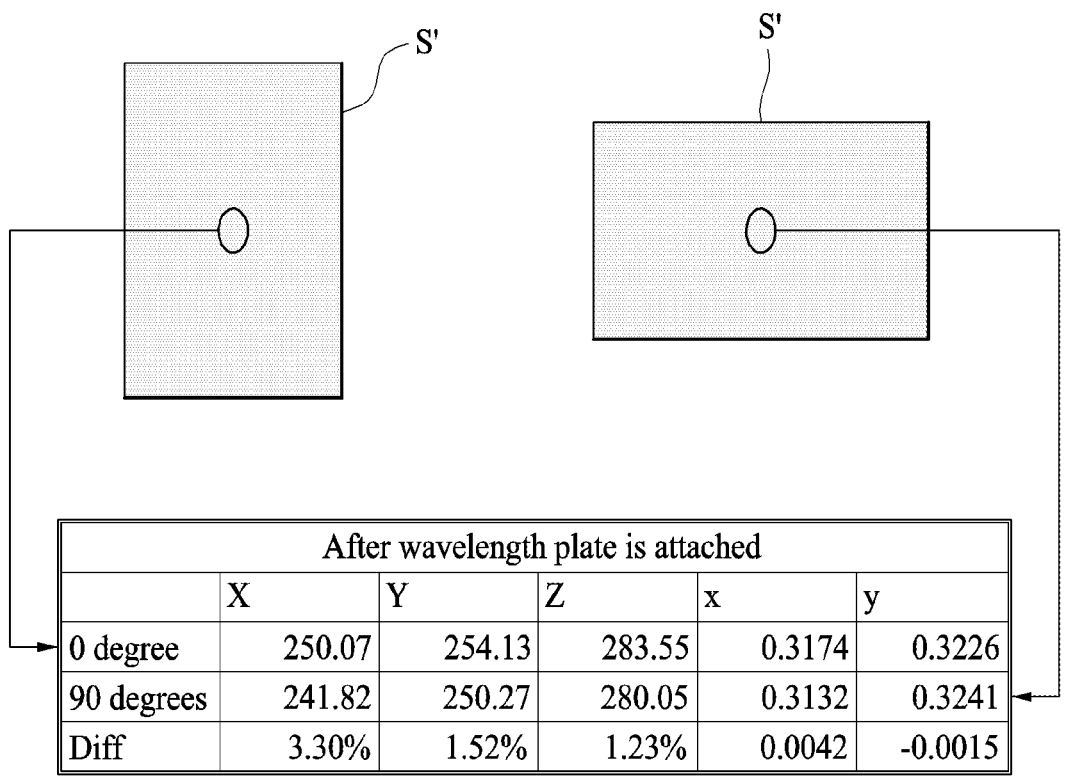
FIG. 6 is a table representing data obtained by measuring tri-stimulus values while arrangement of a subject to be measured is changed, through a brightness colorimeter having a measurement error caused by linearly polarized light, which is corrected, according to the embodiment of the present disclosure.

FIG. 6 is a table representing data obtained by measuring tri-stimulus values while arrangement of a subject to be measured is changed, through a brightness colorimeter having a measurement error caused by linearly polarized light, which is corrected, according to the embodiment of the present disclosure, wherein measured values of tri-stimulus values at the same point are constantly deduced regardless of an arrangement state and an arrangement angle of the display device that is the subject S to be measured.

Figure 7:
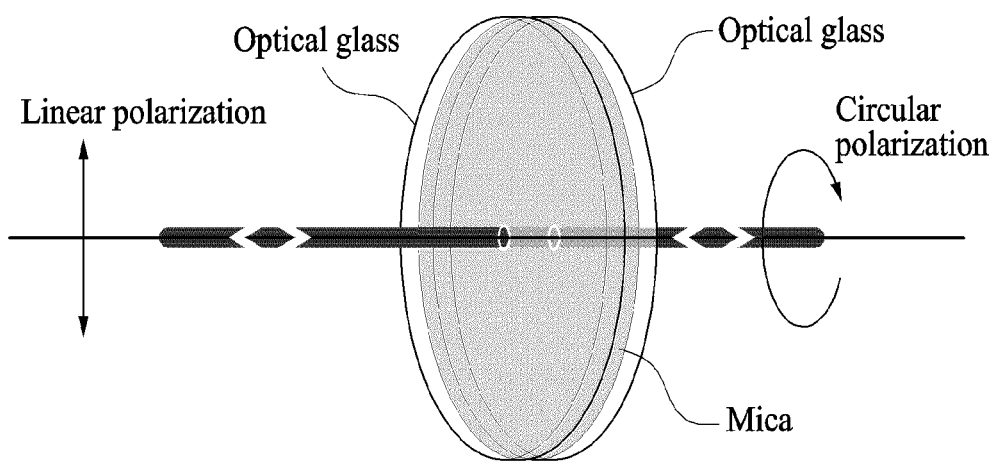
FIG. 7 is a schematic view illustrating characteristics of a quarter wavelength plate, which is included in a brightness colorimeter having a measurement error caused by linearly polarized light, which is corrected, according to the embodiment of the present disclosure.

FIG. 7 is a schematic view illustrating characteristics of a quarter wavelength plate, which is included in a brightness colorimeter having a measurement error caused by linearly polarized light, which is corrected, according to the embodiment of the present disclosure.

Hereinabove, the exemplary embodiments of the present disclosure have described above. It is obvious to those skilled in the corresponding art that the present disclosure may be specified in different specific forms in addition to the above-described embodiments without departing from the purpose and the scope of the present disclosure. Therefore, the above-described embodiments are considered to be not restrictive but illustrative, and accordingly, the present disclosure is not limited to the above descriptions and may be changed within the scope and equivalents of the appended claims.

What is claimed is:

1. A brightness colorimeter having a measurement error caused by linearly polarized light, which is corrected, the brightness colorimeter comprising:
   a lens module to which light irradiated from one side is input;
   a polarization conversion module configured to intersect the light input through the lens module to convert polarization characteristics, the polarization conversion module comprising a wavelength plate configured to convert linearly polarized light into circularly polarized light, the wavelength plate being a quarter wavelength plate having a predetermined thickness such that the linearly polarized light vibrating in directions perpendicular to each other generates an optical path difference of a wavelength of $\lambda/4$;
   a spectral module provided in one unit block to reflect and intersect the light input through the polarization conversion module so as to branch the light in different three directions;
   filter modules arranged on progress paths of the light branched in different three direction through the spectral module to intersect monochromatic light beams having specific spectra among the light branched in the three directions; and measurement modules arranged to correspond to exit angles of the monochromatic light beams passed through the filter modules, to measure at least one of a brightness, a chromaticity, and an error obtained by the monochromatic light beams.

2. The brightness colorimeter of claim 1, wherein the spectral module comprises:

a first spectral body configured to branch input light in different two directions by reflecting and intersecting the input light; and a second spectral body configured to branch the light passed through the first spectral body in different two directions by reflecting and intersecting the light, wherein distances from a point at which the light is input to the first spectral body via different three directions to the filter modules are identical to each other.

3. The brightness colorimeter of claim 1, wherein images obtained by the monochromatic light beams penetrated through the filter modules have measurement errors caused by the linearly polarized light having a same visual range.

4. The brightness colorimeter of claim 1, wherein the filter modules convert the light branched in the three different directions into a spectrum corresponding to an X value, a spectrum corresponding to a Y value and a spectrum corresponding to a Z value among tri-stimulus.

5. The brightness colorimeter of claim 2, wherein when the total amount of the light input to the first spectral body is 1, the total amount of the light branched in different three directions is a third.

6. A brightness colorimeter having a measurement error caused by linearly polarized light, which is corrected, the brightness colorimeter comprising:

a lens module to which light irradiated from one side is input;

a spectral module provided in one unit block to reflect and intersect the light input through the lens module so as to branch the light in different three directions;

polarization conversion modules provided on progress paths of the light branched in different three directions through the spectral module, to intersect the light branched in the different three directions;

filter modules arranged on the progress paths of the light branched in different three directions via the polarization conversion modules, to convert the received light into monochromatic light beams having specific spectra; and measurement modules arranged to correspond to exit angles of the monochromatic light beams passed through the filter modules, to measure at least one of a brightness, a chromaticity, and an error obtained by the monochromatic light beams.

7. The brightness colorimeter of claim 6, wherein each of the polarization conversion modules comprises a wavelength plate configured to convert linearly polarized light into circularly polarized light.

8. The brightness colorimeter of claim 7, wherein the wavelength plate is a quarter wavelength plate having a predetermined thickness such that the linearly polarized light vibrating in directions perpendicular to each other generates an optical path difference of a wavelength of $\lambda/4$.

* * * * *